US006946142B2

(12) United States Patent
Chang et al.

(10) Patent No.: US 6,946,142 B2
(45) Date of Patent: Sep. 20, 2005

(54) MULTI-LAYER PATCHES FOR TEETH WHITENING

(75) Inventors: Sug-Youn Chang, Daejeon (KR); Ji-Young Kim, Daejeon (KR); Jong-Ho Kim, Daejeon (KR); Sei-Young Yun, Seoul (KR)

(73) Assignee: LG Household & Healthcare Ltd., Seoul (KR)

( * ) Notice: Subject to any disclaimer, the term of this patent is extended or adjusted under 35 U.S.C. 154(b) by 247 days.

(21) Appl. No.: 10/177,689

(22) Filed: Jun. 20, 2002

(65) Prior Publication Data

US 2003/0194382 A1 Oct. 16, 2003

Related U.S. Application Data

(60) Provisional application No. 60/324,555, filed on Sep. 25, 2001.

(30) Foreign Application Priority Data

Jun. 23, 2001 (KR) .......................................... 2001-36024
Jul. 4, 2001 (KR) .......................................... 2001-39847

(51) Int. Cl.$^7$ .............................. A61K 7/16; A61K 7/20
(52) U.S. Cl. ........................... 424/435; 424/49; 424/53; 424/401; 424/443; 424/447; 424/448; 424/449
(58) Field of Search ............................. 424/49–88, 448, 424/449

(56) References Cited

U.S. PATENT DOCUMENTS

| | | | |
|---|---|---|---|
| 4,517,173 A | 5/1985 | Kizawa et al. | |
| 4,668,232 A | * 5/1987 | Cordes et al. | 424/448 |
| 4,696,757 A | 9/1987 | Blank et al. | |
| 4,713,243 A | 12/1987 | Schiraldi et al. | |
| 4,728,291 A | 3/1988 | Golub | |
| 4,741,700 A | 5/1988 | Barabe | |
| 4,741,941 A | 5/1988 | Englebert | |
| 4,786,253 A | 11/1988 | Morais | |
| 4,799,888 A | 1/1989 | Golub | |
| 4,812,308 A | 3/1989 | Winston | |
| 4,839,156 A | 6/1989 | Ng | |
| 4,839,157 A | 6/1989 | Mei-King | |
| RE33,093 E | 10/1989 | Schiraldi et al. | |
| 4,891,211 A | 1/1990 | Winston | |
| 4,895,721 A | 1/1990 | Drucker | |
| 4,900,552 A | * 2/1990 | Sanvordeker et al. | 424/422 |
| 4,900,554 A | 2/1990 | Yanagibaski | |
| 4,919,615 A | 4/1990 | Croll | |
| 4,933,182 A | 6/1990 | Higashi et al. | |
| 4,983,379 A | 1/1991 | Schaeffer | |
| 4,983,380 A | 1/1991 | Yarborough | |
| 5,000,940 A | 3/1991 | Staples | |
| 5,008,106 A | 4/1991 | Merianos | |
| 5,009,885 A | 4/1991 | Yarborough | |
| 5,032,178 A | 7/1991 | Cornell | |
| 5,041,280 A | 8/1991 | Smigel | |
| 5,055,287 A | 10/1991 | Kessler | |
| 5,059,417 A | 10/1991 | Williams | |
| 5,084,268 A | 1/1992 | Thaler | |
| 5,098,303 A | 3/1992 | Fischer | |
| 5,110,583 A | 5/1992 | Sampathkumar | |
| 5,122,365 A | 6/1992 | Murayama | |
| 5,128,122 A | 7/1992 | Cerami | |
| 5,130,124 A | 7/1992 | Merianos | |
| 5,166,233 A | 11/1992 | Kuroya | |
| 5,171,564 A | 12/1992 | Nathoo et al. | |
| RE34,196 E | 3/1993 | Munro | |
| 5,192,532 A | 3/1993 | Guay | |
| 5,208,010 A | 5/1993 | Thaler | |
| 5,217,710 A | 6/1993 | Williams | |
| 5,234,342 A | 8/1993 | Fischer | |
| 5,234,957 A | 8/1993 | Mantelle | |
| 5,240,415 A | 8/1993 | Haynie | |
| 5,256,402 A | 10/1993 | Prencipe et al. | |
| 5,279,816 A | 1/1994 | Church | |
| 5,281,412 A | 1/1994 | Lukacovic | |
| 5,290,566 A | 3/1994 | Schow | |
| 5,292,502 A | 3/1994 | Burke et al. | |
| 5,302,375 A | 4/1994 | Viscio | |
| 5,326,685 A | 7/1994 | Gaglio | |
| 5,332,576 A | 7/1994 | Mantelle | |
| 5,340,314 A | 8/1994 | Tarvis | |
| 5,340,581 A | 8/1994 | Tseng | |
| 5,348,734 A | 9/1994 | Ratcliff | |
| 5,366,285 A | 11/1994 | Borgen et al. | |
| 5,372,802 A | 12/1994 | Barrows | |
| 5,376,006 A | 12/1994 | Fischer | |
| 5,380,198 A | 1/1995 | Suhonen | |
| 5,401,495 A | 3/1995 | Murayama | |
| 5,409,631 A | 4/1995 | Fischer | |
| 5,425,953 A | 6/1995 | Sintov | |
| 5,437,858 A | 8/1995 | Hungerbach | |

(Continued)

FOREIGN PATENT DOCUMENTS

| | | |
|---|---|---|
| GB | 2108841 | 5/1983 |
| JP | 10017448 | 1/1998 |
| WO | WO 99/62472 | 12/1999 |
| WO | 99/62472 | * 12/1999 |
| WO | WO 01168045 | 9/2001 |

OTHER PUBLICATIONS

U.S. Appl. No. 10/445,589, filed May 27, 2003 (and Preliminary Amendment) filed May 27, 2003 entitled Patches for Whitening Teeth; 41 pp.
U.S. Appl. No. 10/717,226, Apparatus and Method for Whitening Teeth, filed on Nov. 19, 2003 (pp. 74).

*Primary Examiner*—Frederick Krass
(74) *Attorney, Agent, or Firm*—Fox Rothschild LLP

(57) ABSTRACT

The present invention relates to a dry type teeth whitening patch with a multi-layer structure of three or more layers. More particularly, in the dry type patch, a contact adhesive layer substantially free of peroxide comprises a hydrophilic glass polymer as a base polymer so that it provides substantial adhesive strength when hydrated by water, an active material reservoir layer comprises peroxide as a teeth whitening agent, and a backing layer which is impermeable to water. The dry type patch of the present invention has superior teeth whitening effect and excellent peroxide stability at a high temperature since the peroxide-containing layer is covered and protected by other layers.

22 Claims, No Drawings

U.S. PATENT DOCUMENTS

| | | | | |
|---|---|---|---|---|
| 5,438,076 A | | 8/1995 | Friedman | |
| 5,505,956 A | * | 4/1996 | Kim et al. | 424/448 |
| 5,536,285 A | | 7/1996 | Isaksson et al. | |
| 5,560,379 A | | 10/1996 | Pieczenik | |
| 5,565,190 A | | 10/1996 | Santalucia | |
| 5,575,654 A | | 11/1996 | Fontenot | |
| 5,611,687 A | | 3/1997 | Wagner | |
| 5,614,174 A | | 3/1997 | Hsu | |
| 5,620,322 A | | 4/1997 | Lococo | |
| 5,626,866 A | | 5/1997 | Ebert | |
| 5,631,000 A | | 5/1997 | Pellico | |
| 5,631,055 A | | 5/1997 | Vines | |
| 5,648,064 A | | 7/1997 | Gaffar | |
| 5,683,680 A | | 11/1997 | Santalucia | |
| 5,689,182 A | | 11/1997 | Togo | |
| 5,700,478 A | * | 12/1997 | Biegajski et al. | 424/434 |
| 5,707,611 A | | 1/1998 | Ikemura | |
| 5,707,736 A | | 1/1998 | Levy | |
| 5,713,738 A | | 2/1998 | Yarborough | |
| 5,718,886 A | | 2/1998 | Pellico | |
| 5,723,132 A | | 3/1998 | Tseng | |
| 5,725,843 A | | 3/1998 | Fischer | |
| 5,746,598 A | | 5/1998 | Fischer | |
| 5,766,574 A | | 6/1998 | Christina-Beck | |
| 5,770,105 A | | 6/1998 | Fischer | |
| 5,770,182 A | | 6/1998 | Fischer | |
| 5,776,437 A | | 7/1998 | Burgess | |
| 5,785,527 A | | 7/1998 | Jensen | |
| 5,785,957 A | | 7/1998 | Losee | |
| 5,814,303 A | | 9/1998 | Williams | |
| 5,814,304 A | | 9/1998 | Wong et al. | |
| 5,820,822 A | | 10/1998 | Kross | |
| 5,820,852 A | | 10/1998 | Burgess | |
| 5,820,854 A | | 10/1998 | Glandorf | |
| 5,846,570 A | | 12/1998 | Barrow | |
| 5,849,269 A | | 12/1998 | Burgess | |
| 5,851,514 A | | 12/1998 | Hassan | |
| 5,855,875 A | | 1/1999 | Williams | |
| 5,858,332 A | | 1/1999 | Jensen | |
| 5,863,202 A | | 1/1999 | Fontenot et al. | |
| 5,879,691 A | | 3/1999 | Sagel et al. | |
| 5,885,553 A | | 3/1999 | Michael | |
| 5,885,554 A | | 3/1999 | Michael | |
| 5,891,453 A | * | 4/1999 | Sagel et al. | 424/53 |
| 5,894,017 A | | 4/1999 | Sagel et al. | |
| 5,902,568 A | | 5/1999 | Ryles | |
| 5,908,614 A | | 6/1999 | Montgomery | |
| 5,914,118 A | * | 6/1999 | Yamamura et al. | 424/402 |
| 5,915,969 A | | 6/1999 | Linden | |
| 5,922,307 A | | 7/1999 | Montgomery | |
| 5,928,628 A | | 7/1999 | Pellico | |
| 5,932,193 A | | 8/1999 | Lopez | |
| 5,945,032 A | | 8/1999 | Breitenbach | |
| 5,980,249 A | | 11/1999 | Fontenot | |
| 5,985,249 A | | 11/1999 | Fischer | |
| 5,989,569 A | | 11/1999 | Dirksing et al. | |
| 6,007,795 A | | 12/1999 | Masterman | |
| 6,017,515 A | | 1/2000 | van den Bosch | |
| 6,022,528 A | | 2/2000 | Waterfield | |
| 6,030,222 A | | 2/2000 | Tarver | |
| 6,036,493 A | | 3/2000 | Sharma | |
| 6,036,943 A | | 3/2000 | Fischer | |
| 6,045,811 A | | 4/2000 | Dirksing et al. | |
| 6,072,100 A | * | 6/2000 | Mooney et al. | 424/448 |
| 6,080,811 A | * | 6/2000 | Schehlmann et al. | 433/229 |
| 6,083,421 A | | 7/2000 | Huang | |
| 6,086,855 A | | 7/2000 | Fischer | |
| 6,096,328 A | | 8/2000 | Sagel et al. | |
| 6,106,293 A | | 8/2000 | Wiesel | |
| 6,110,446 A | | 8/2000 | Prencipe | |
| 6,121,213 A | | 9/2000 | Vergara | |
| 6,136,297 A | | 10/2000 | Sagel et al. | |
| 6,149,895 A | | 11/2000 | Kutsch | |
| 6,155,832 A | | 12/2000 | Wiesel | |
| 6,174,516 B1 | | 1/2001 | Curtis | |
| 6,190,689 B1 | * | 2/2001 | Hoffmann et al. | 424/448 |
| 6,197,331 B1 | * | 3/2001 | Lerner et al. | 424/448 |
| 6,221,341 B1 | | 4/2001 | Montgomery | |
| 6,241,973 B1 | | 6/2001 | Rinne | |
| 6,274,122 B1 | | 8/2001 | McLaughlin | |
| 6,277,458 B1 | | 8/2001 | Dirksing et al. | |
| 6,280,708 B1 | | 8/2001 | Ryles et al. | |
| 6,284,152 B1 | | 9/2001 | Kross | |
| 6,290,934 B1 | | 9/2001 | Kramer | |
| 6,290,935 B1 | | 9/2001 | Masters | |
| 6,306,370 B1 | | 10/2001 | Jensen | |
| 6,309,622 B1 | | 10/2001 | Watkings | |
| 6,309,625 B1 | | 10/2001 | Jensen | |
| 6,312,666 B1 | | 11/2001 | Oxman | |
| 6,312,670 B1 | | 11/2001 | Montgomery | |
| 6,312,671 B1 | | 11/2001 | Jensen | |
| 6,319,510 B1 | * | 11/2001 | Yates | 424/443 |
| 6,322,773 B1 | | 11/2001 | Montgomery | |
| 6,322,774 B1 | | 11/2001 | Jensen | |
| 6,325,997 B1 | | 12/2001 | Christopfel | |
| 6,331,291 B1 | | 12/2001 | Glace | |
| 6,331,292 B1 | | 12/2001 | Montgomery | |
| 6,342,206 B1 | | 1/2002 | Gopalkrishnan | |
| 6,348,187 B1 | | 2/2002 | Pan | |
| 6,350,437 B1 | | 2/2002 | Pasetti | |
| 6,350,438 B1 | | 2/2002 | Witt | |
| 6,365,134 B1 | | 4/2002 | Orlowski | |
| 6,368,576 B1 | | 4/2002 | Jensen | |
| 6,375,933 B1 | | 4/2002 | Subramanyam | |
| 6,379,653 B1 | | 4/2002 | Aaslyng | |
| 6,391,283 B1 | | 5/2002 | Jensen | |
| 6,391,286 B1 | | 5/2002 | Mitra | |
| 6,403,060 B1 | | 6/2002 | Bornstein | |
| 6,409,992 B1 | | 6/2002 | Kleinberg | |
| 6,409,993 B1 | | 6/2002 | Jensen | |
| 6,409,994 B1 | | 6/2002 | Dahlin | |
| 6,413,502 B1 | | 7/2002 | Bornstein | |
| 6,419,902 B1 | | 7/2002 | Wright | |
| 6,419,905 B1 | | 7/2002 | Alvarez Hernandez | |
| 6,419,906 B1 | | 7/2002 | Xu et al. | |
| 6,423,300 B1 | | 7/2002 | Kleinberg | |
| 6,435,873 B1 | * | 8/2002 | Burgio | 433/80 |
| 6,440,396 B1 | | 8/2002 | McLaughlin | |
| 6,440,749 B1 | | 8/2002 | Cerami | |
| 6,447,757 B1 | | 9/2002 | Orlowski | |
| 6,457,469 B1 | | 10/2002 | Mueller | |
| 6,458,340 B1 | | 10/2002 | Ibsen | |
| 6,458,380 B1 | * | 10/2002 | Leaderman | 424/49 |
| 6,471,947 B2 | | 10/2002 | Bhakoo | |
| 6,475,472 B2 | | 11/2002 | Joiner | |
| 6,479,037 B1 | | 11/2002 | Montgomery | |
| 6,485,709 B2 | | 11/2002 | Banerjee | |
| 6,488,913 B2 | | 12/2002 | Orlowski | |
| 6,488,914 B2 | | 12/2002 | Montgomery | |
| 6,500,408 B2 | * | 12/2002 | Chen | 424/53 |
| 6,503,485 B1 | | 1/2003 | Allred | |
| 6,503,486 B2 | | 1/2003 | Xu | |
| 6,509,007 B2 | | 1/2003 | Rajaiah | |
| 6,514,483 B2 | | 2/2003 | Xu | |
| 6,514,484 B2 | | 2/2003 | Rajaiah | |
| 6,517,350 B2 | * | 2/2003 | Diasti et al. | 424/53 |
| 6,682,721 B2 | * | 1/2004 | Kim et al. | 424/53 |
| 6,689,344 B2 | * | 2/2004 | Chang et al. | 424/53 |
| 6,780,401 B2 | * | 8/2004 | Kim et al. | 424/53 |
| 2002/0081555 A1 | | 6/2002 | Wiesel | |

* cited by examiner

MULTI-LAYER PATCHES FOR TEETH WHITENING

This application claims the benefit under 35 U.S.C. §119 of U.S. provisional patent application No. 60/324,555 filed Sep. 25, 2001 which is hereby incorporated by reference in its entirety for all purposes.

TECHNICAL FIELD

The present invention relates to a dry type patch that removes stains from teeth and whitens teeth only through attachment to the teeth. More particularly, it relates to a dry type patch comprising a peroxide, known as an excellent teeth whitening agent, which is capable of remaining in the attached site for a desired period of time, thereby achieving a teeth whitening effect in a short period of time. In particular, the dry type patch of the present invention consists of a multi-layer structure having three or more layers, which has excellent adhesive strength and peel-off property, and is thereby convenient to use. Further, it has good stability at high temperatures and good ability to maintain shape during storage, which makes it comfortable to carry. In addition, due to the dry nature of the patch, the peroxide-containing layer does not stick to the user's hands or face during the process of its attachment to the teeth. Further, since the patch comprises three or more layers, the peroxide-containing layer is covered with and protected by other layers, which improves its safety to human tissue.

BACKGROUND OF THE INVENTION

As people's interest in whitening their teeth increases, a number of toothpastes having teeth whitening effect have become commercially available. However, even though the toothpaste contains a teeth whitening agent having good performance, it is hard to achieve significant whitening effect in a short period of time by brushing teeth with only 1 to 3 minutes of contact time between teeth and toothpaste.

Recently, in order to solve the above problems, a number of patent applications related thereto have been filed and teeth whitening products of various formulations have appeared on the market.

For example, in the case of professional whitening gel, a dentist manufactures an individualized mouth tray, which precisely fits the teeth of the patient. The patient applies the whitening gel in a prescribed amount to inner walls and trough of the tray following instructions at home. Therefore, this whitening method has disadvantages in terms of convenience and cost. Furthermore, this method may present problems with safety and comfort, since the surplus peroxide gel and the mouth tray itself may cause irritation or damage to the gums or oral cavity.

In order to solve these problems, Japanese Patent No. 10,017,448, assigned to Lion Corp., discloses a sheet-shaped oral plaster, which comprises a teeth adhesive layer and supporting layer. A whitening agent used in the plaster includes kojic acid and derivatives thereof, ascorbic acid and derivatives thereof, carbamide peroxide and the like, among which kojic acid and various salts thereof are described as being effective. However, the above-mentioned whitening agents have a strong acidity, which may cause irritation to oral cavity. Further, since these agents effect whitening at a high acidity, it is difficult to produce good whitening without irritation. When this two-layer patch structure contains a high reactivity material such as a whitening agent, its stability degrades at high temperatures even though being stored with a release liner attached.

U.S. Pat. Nos. 5,879,691, 5,891,453 and 5,989,569, and WO 98/55044, assigned to Procter & Gamble, disclose a delivery system for a teeth whitener, comprising a thin, transparent and flexible polyethylene strip having a professional whitening gel thereon, wherein the professional whitening gel is pre-coated during the manufacturing process or applied to the strip or teeth directly before the attachment to the teeth. Since it does not use a mouth tray, the usage is facilitated and improved. Further, because the strip is thin and transparent, its use does not present an obstacle to the daily life. However, the delivery system disclosed therein is a wet type whitening layer constructed by using a teeth whitening substance along with a gelling agent, preferably carboxypolymethylene, obtained from B. F. Goodrich Company under the trade name of Carbopol, water, pH adjusting agent and additive carrier materials and applying the resultant highly viscous gel onto a strip of flexible polyethylene strip. When attaching and wearing the system onto teeth, the teeth whitening gel containing high concentration peroxide may adhere to and remain on hands, tongue, gums and the like. That is, such wet type gel systems have room for improvement in terms of handling. Further, in the two-layer embodiment consisting of a teeth whitening substance and strip, the peroxide stability is not sufficiently assured and the whitening effect may be diminished when stored at a high temperature or for a long period of time.

U.S. Pat. Nos. 5,310,563 and 5,639,445, assigned to Colgate-Palmolive Company, disclose a dental formulation comprising an active component dispersed in a polysiloxane polymer composition, available under the trade name of Dow Corning 3179 Dilatant Compound by Dow Corning Corporation, which is attached to the teeth by pressing it against the teeth and gum, and is easily removed from the teeth. The two-layer embodiment has the active whitening component encapsulated in the polymer. Therefore, the stability of the active peroxide component can be improved to some degree. However, this product has a disadvantage in that the active ingredient cannot be easily released from the Dilatant Compound in a short period of time, and consequently, an extended contact time is required to obtain the desired teeth whitening effect.

Therefore, there is a need for a dry type teeth whitening patch, which has improved peroxide stability at high temperature and safety to the human tissue during its attachment to the teeth.

SUMMARY OF THE INVENTION

The present invention relates to a dry type teeth whitening patch with a multi-layer structure of three or more layers. More particularly, in the dry type patch, a contact adhesive layer substantially free of peroxide comprises a hydrophilic glass polymer as a base polymer so that it provides substantial adhesive strength when hydrated by water, an active material reservoir layer comprises peroxide as a teeth whitening agent, and a backing layer which is impermeable to water. The dry type patch of the present invention has superior teeth whitening effect and excellent peroxide stability at a high temperature since the peroxide-containing layer is covered and protected by other layers.

A dry type patch for whitening teeth having a multi-layer structure of three or more layers is disclosed. The patch comprises a contact adhesive layer, a backing layer, and an active material reservoir layer comprising a peroxide, a peroxide stabilizer, and a hydrophilic glass polymer and is positioned between the contact adhesive layer and the backing layer. The contact adhesive layer is substantially free of peroxide and comprises a hydrophilic glass polymer as a base polymer such that the contact adhesive layer provides substantial adhesive attachment to the teeth when hydrated by water and placed in contact with the teeth and has insubstantial adhesiveness before hydration and attachment to the teeth. The active material reservoir layer releases peroxide contained therein subsequent to the hydration and attachment of the contact adhesive layer to the teeth.

In another preferred embodiment, the active material reservoir layer is substantial free of peroxide stabilizer and the hydrophilic glass polymer is selected from the group consisting of polyvinyl pyrrolidone-vinyl acetate copolymer, polyethylene oxide, polyvinyl pyrrolidone, Polyquaterium-11, Polyquaterium-39 and combinations thereof and formulated with a solvent selected from the group consisting of a mixture of water and ethanol in a ratio of 9:1 to 0:10, ethyl acetate, methylene chloride, isopropyl alcohol, acetonitrile, and mixtures thereof.

DETAILED DISCLOSURE OF THE INVENTION

Therefore, it is an object of the present invention to provide a dry type teeth whitening patch, which provides sufficient contact time between teeth whitening agent and stains on surfaces of teeth, thereby achieving a teeth whitening effect in a short period of time.

It is another object of the present invention to provide a dry type teeth whitening patch which is safe when a user removes the patch from the release liner with his hands and fingers to attach it to the surface of his teeth, and to provide a patch where, when the patch is hydrated by moisture on the surface of the teeth, a contact adhesive layer which does not contain the teeth whitening agent acquires strong adhesiveness and subsequently, an active material reservoir layer hydrates and begins to release the whitening agent.

It is a still another object of the present invention to provide a dry type teeth whitening patch which has a good peroxide stability at a high temperature, wherein the active material reservoir layer containing peroxide, which is a whitening agent having a high reactivity, is protected by a contact adhesive layer.

It is a further object of the present invention to provide a dry type teeth whitening patch which has excellent adhesive strength and peel-off properties, and is comfortable during use and, thereby is convenient to use.

It is a still further object of the present invention to provide a dry type teeth whitening patch in which the peroxide-containing layer does not stick to hands or face during the process of its attachment to the teeth and the peroxide-containing layer is protected by other layers, thereby being safe to the human body.

The above and other objects are accomplished by a dry type teeth whitening patch of the present invention having multi-layer structure of three or more layers comprising a contact adhesive layer, an active material reservoir layer and a backing layer, in which the contact adhesive layer contains no teeth whitening agent, the contact adhesive layer comprises a hydrophilic glass polymer as a base polymer so that it may have substantial adhesive strength when hydrated by water upon attachment to the teeth while having little or no adhesiveness before attachment to the teeth and subsequently, the active material reservoir layer under the contact adhesive layer begins to be hydrated and releases peroxide contained therein as a teeth whitening agent, the active material reservoir layer contains a peroxide stabilizer along with the peroxide, and the active material reservoir layer is protected by one or more of the contact adhesive layer and the backing layer, thereby providing good peroxide stability.

The present invention provides a novel dry type teeth whitening patch comprising peroxide as a teeth whitening agent. In particular, the present invention provides a dry type teeth whitening patch which has a multi-layer structure of three or more layers comprising a contact adhesive layer which is substantially devoid of teeth whitening agent and consists essentially of a hydrophilic glass polymer, an active material reservoir layer which contains a peroxide as a teeth whitening agent and a backing layer, wherein when the patch is hydrated in a moist oral cavity the contact adhesive layer acquires strong adhesive strength and the active material reservoir layer also begins to be dissolved, thereby releasing the teeth whitening agent.

The dry type patch according to the present invention is convenient to use and, as compared to a conventional wet type patch, it is characterized in that the active material does not stick to the user's skin when the patch touches the hands or face. Such advantage may be accomplished by a two-layer patch where it is manufactured as a dry type patch. However, in the patch having a multi-layer structure of three or more layers according to the present invention, peroxide does not contact the user's skin during the process of its attachment to the teeth, because the active material reservoir layer containing peroxide is protected by one or more layers. Further, the dry type patch according to the present invention has excellent adhesive strength after being hydrated, so that, there is no difficulty in laughing and talking, and attachment to the teeth can be maintained for an extended period of time to assure enough contact time between the tooth whitening agent in the patch and stains on the teeth, thereby promoting rapid teeth whitening effect.

The conventional patches for teeth whitening comprising peroxide usually have a two-layer structure of an adhesive layer and a backing layer. The adhesive layer includes a teeth whitening agent and adhesive material. However, highly adhesive polymers generally used in the adhesive layer are poorly compatible with peroxide. Such problems could be solved to some degree by constructing the patch as a dry type instead of wet type patch and using a polymer compatible with peroxide or a peroxide stabilizer. However, there still remains a demand for improving the peroxide stability at a high temperature. The present inventors provide a novel dry type patch consisting of multi-layer structure of three or more layers.

According to the present invention, there is provided a dry type teeth whitening patch consisting of multi-layer structure of three or more layers comprising a contact adhesive layer, an active material reservoir layer and a backing layer. The contact adhesive layer contains no teeth whitening agent and comprises a hydrophilic glass polymer. The active material reservoir layer comprises peroxide as a teeth whitening agent and polymers having a good compatibility with peroxide. Alternatively, the active material reservoir layer comprises a polymer which has low compatibility with peroxide but enables peroxide to be stable at a high temperature when used with a peroxide stabilizer. Further, the backing layer is preferably impermeable to water in a manner similar to conventional two-layer patches. In the teeth whitening patch according to the present invention having multi-layer structure of three or more layers, the active material reservoir layer containing peroxide can be protected and the peroxide stability is improved. Further, even when a release liner is not provided, the active material reservoir layer containing peroxide is not exposed to the air, thereby being safe and stable The dry type teeth whitening patch according to the present invention may further comprise a peroxide activator in the contact adhesive layer, along with a protective layer between the contact adhesive layer and the active material reservoir layer containing peroxide. In this embodiment, peroxide does not directly contact the peroxide activator in the formulation. It is only when the patch is in use in the oral cavity that the peroxide activator promotes the whitening effect of peroxide to accomplish whitening effect in a short time period.

According to the present invention, there is also provided an embodiment wherein the contact adhesive layer contains no peroxide activator, a second layer contains a peroxide activator optionally along with other whitening agents such as papain or pyrophosphate, a third layer serves as protective layer, and a fourth becomes an active material reservoir layer containing peroxide.

In general, patches used for medical purpose are divided into two categories: a wet type and a dry type. The wet type patch is, for example, a hydrogel formulation, or a formulation formed by applying a gel to a backing layer or immersing the backing layer in a solution. This type of patch is characterized in that the initial state of the formulation is wet since content of water or humectant in the formulation is high. Meanwhile, the dry type patch is characterized in that the initial state of the formulation is dry since it is prepared by dry process and the water or humectant content in the formulation is low. For delivering a moisturizer or other medicinal components to dry skin, the wet type patch is preferable due to its high content of water and flexibility. However, the wet type patch generally lacks adhesive strength.

The wet type patch is manufactured by applying a gel to the backing layer or immersing the backing layer in a solution. A considerable amount of the gel layer may easily stick to the user's skin even when it briefly touches the skin during attachment to the teeth. Therefore, the wet type patch is inconvenient to use and lacks safety. Moreover, a medicinal agent or a gel comprising a teeth whitening agent may sometimes pass through a supporting layer toward the opposite side thereof. Especially, when a high concentration of peroxide is coated with a gel containing a large amount of humectant, the peroxide may stick to undesired sites, such as hands, lips, gums, etc., causing irritation. Further, if the humectant remains on the tongue, the user may have an unpleasant feeling.

Therefore, in order to solve the above-described problems involved with wet type patches, the present inventors adopt a dry type patch with a novel formulation. The dry type patch according to the present invention has advantages in that it has sufficient adhesive strength in a moist oral cavity while preventing the teeth whitening agent from adhering to hands or other places such as gums and tongue in the oral cavity, thereby reducing any unpleasant feeling while being worn by the user.

In order to produce such a dry type patch, it is necessary to select a polymer, which is able to acquire adhesiveness or strengthen its adhesiveness when hydrated by a small quantity of water at a desired place while having little or no adhesiveness in a dry state. Also, the polymer should begin to release a teeth whitening agent upon hydration. The inventors have discovered that hydrophilic glass polymers have such properties and thus accomplished the present invention by employing hydrophilic glass polymer as a base polymer in a contact adhesive layer.

The active material reservoir layer may contain such hydrophilic polymer as used in the contact adhesive layer so that when hydrated by saliva it releases peroxide, after the contact adhesive layer is hydrated. Alternatively, the active material reservoir layer may contain such materials that are soluble in water and have good adhesiveness to the teeth and good compatibility with peroxide. For instance, shellac releases an active material contained therein when it is dissolved in water.

As the last layer, a backing layer contains water-insoluble and water-impermeable polymer as a film former in order to prevent the patch from sticking to gums or tongue and from deforming or being detached from teeth by saliva.

The teeth whitening effect may be controlled by adjusting the thickness of patch or by varying active ingredients. Since the patch according to the present invention is transparent, it is possible for user to observe oxygen bubbles generated by peroxide upon bleaching teeth or removing stains while wearing the patch, and thereby to visibly recognize the whitening effect. Also, the patch strip is transparent and not conspicuous upon wearing, so that the user's daily life is not affected.

The matrix type patch of the present invention is intended to be attached not to skin or mucous membrane, but to the enamel layer of teeth so as to supply a teeth whitening agent to a surface of teeth for a sufficient time to whiten the teeth. The principle for providing that the patch is attached to teeth and a whitening agent contained in the matrix is released onto the surface of teeth is described below.

In the field of transdermal drug delivery systems with time lag, there has been suggested a transdermal formulation using moisture transpired from skin to release a drug when a predetermined time passes after its attachment. More particularly, a barrier impermeable to the drug is provided between drug reservoir and skin adhesion surface in the transdermal formulation When the formulation is attached to skin, the barrier is gradually hydrated by moisture transpired from the skin, whereby its permeability to drug is increased. In this case, a hydrophilic glass polymer is used as the barrier material.

The present inventors used a hydrophilic glass polymer in a contact adhesive layer of a matrix type patch so that the adhesive layer acquires adhesiveness or strengthens its adhesiveness when hydrated by moisture on the teeth while having little or no adhesive strength when stored or handled with hands to be attached to the teeth. Most of such glass polymers, when hydrated, provide sufficient adhesive strength to enable the patch to be fixed at the contact site of the teeth surface. Thus, according to the present invention, no additional means for fixing the patch to the teeth is required to attain sufficient contact time between the whitening agent and teeth, such as a marginal adhesive strip to be folded onto the back side of teeth. Once the contact adhesive layer is hydrated to have adhesive strength, the active material reservoir layer is subsequently hydrated and begins to release a teeth whitening agent.

The patch of the present invention does not generate significant irritation of gums or skin in the oral cavity even though it directly contacts with them since it contains a small amount of whitening agent. In addition, the patch of the present invention is attachable to teeth only, so that whitening agent is not released onto gums.

Thus, the dry type patch according to the present invention provides the above features by comprising multi-layer structure of three or more layers, wherein the contact adhesive layer contains a hydrophilic glass polymer, the active material reservoir layer contains peroxide and the backing layer is impermeable to water.

For these purposes, the polymers which can be used in the contact adhesive layer of the patch according to the present invention include polyalkylvinyl ether-maleic acid copolymer (PVM/MA copolymer) such as Gantrez AN 119, AN 139 and S-97, polyvinyl alcohol, polyacrylic acid, Poloxamer 407 (Pluronic), polyvinyl pyrrolidone-vinyl acetate copolymer (PVP/VA copolymer) such as Luviskol VA and Plasdone S PVP/VA, polyethylene oxide (Polyox), polyvinyl pyrrolidone (PVP, K-15~K-120), Polyquaterium-11 (Gafquat 755N), Polyquaterium-39 (Merquat plus 3330), carboxypolymethylene (Carbopol), hydroxypropylmethyl cellulose, hydroxyethyl cellulose, hydroxypropyl cellulose, gelatin and alginate salt such as sodium alginate. The above-described polymers can be used alone or in mixtures thereof. Solvents for these polymers includes water, ethanol or mixtures thereof. Further, other organic solvents such as ethyl acetate, methylene chloride, isopropyl alcohol, acetonitrile or mixtures thereof with varied ratios may be also used as a solvent.

The patch to be attached onto teeth should be flexible enough to be deformable so that it conforms to contours of teeth. Since some polymers have a poor flexibility, suitable plasticizers may be added. Polypropylene glycol, glycerin, polyethylene glycol are generally used as the plasticizers.

For the active material reservoir layer containing peroxide, all the hydrophilic polymers which may be used in the contact adhesive layer are preferably used. In addition, shellac, a polymer used as enteric coating material, which is soluble in water at pH 6 or higher and is compatible with peroxide, can be used in the active material reservoir layer.

The above-described hydrophilic polymers may be used in the contact adhesive layer or other layers which contain no peroxide, without affecting the stability of peroxide. Considering the peroxide stability at a high temperature in the patch formulation, however, a hydrophilic glass polymer which is compatible with peroxide is preferably used in the active material reservoir layer containing peroxide.

Hydrophilic glass polymers such as polyvinyl pyrrolidone (PVP, K-15~K-120), polyquaternium-11, polyquaternium-39, polyvinyl pyrrolidone-vinyl acetate copolymer (PVP/VA copolymer) have good compatibility with peroxide and are easily soluble in water, ethanol or mixtures thereof. They also have good solubility in organic solvents. Accordingly, peroxide in the patch can be stabilized by using organic solvents alone or mixed with water, for example, by using the mixture of water and ethanol in the ratio of 9:1 to 0:10, without using a stabilizer therefor. Polyethylene oxide, which is not soluble in ethanol but easily soluble in water or other organic solvents, has good compatibility with peroxide.

Polyvinyl pyrrolidone (PVP) is the most preferred hydrophilic glass polymer to be used in the active material reservoir layer containing peroxide. It is believed that the good compatibility of polyvinyl pyrrolidone with peroxide results from the stabilization of peroxide by formation of complexes with polyvinyl pyrrolidone via hydrogen bonding. Among the available PVP, K-15~K-120 are used, and K-90 (PVP) is preferably used in the patch of the present invention. K-30 (PVP) is more preferable since higher gel content is desired in the efficiency upon producing by casting method. Preferably, the PVP has a relatively high molecular weight, preferably greater then about 500,000, more preferably greater than about 1,000,000. In a preferred embodiment, PVP having a molecular weight of 1,270,000 is used. Further, peroxides are found to be compatible with polymers having quaternary ammonium structure, such as polyquaternium.

According to the present invention, an organic solvent or mixtures of water and ethanol are used as solvent for adhesive materials. Glass polymers which are highly compatible with peroxide are typically so hydrophilic that they cannot be uniformly coated on the surface of release liner or other sheet. An organic solvent or mixtures of water and ethanol can solve such problem so as to form a uniform sheet layer. When the above-mentioned polymers which are highly compatible with peroxide are used, sufficient peroxide stability is obtained without using a stabilizer in the active material reservoir layer.

The active material reservoir layer also has plasticizer for the same reason as in the contact adhesive layer. Although a suitable plasticizer may vary according to the polymer used, polypropylene glycol, glycerin, polyethylene glycol are generally used.

When a polymer of low compatibility with peroxide is used in the active material reservoir layer, a stabilizer is preferably added to overcome the expected problems. A peroxide stabilizer in the formulation is one or more selected from the group consisting of alkylaryl sulphonates, alkyl sulphonates, alkyl carboxylates, alkyldiphenyloxide disulphonates, a series of Span such as Span 20 (sorbitan monolaurate), Span 40 (sorbitan monopalmitate), Span 60 (sorbitan monostearate), Span 80 (sorbitan monooleate) and Span 85 (sorbitan trioleate), POE sorbitan fatty acid esters (TWEEN), glycerin fatty acid esters, esters, organic acid monoglycerides, sodium stearyl lactates and polysorbates.

The teeth whitening agent contained in the active material reservoir layer may be selected from a group consisting of hydrogen peroxide, carbamide peroxide, calcium peroxide, sodium percarbonate, sodium perborate, tetrasodium pyrophosphate peroxidate and mixtures thereof.

Generally, in the two-layer patch having an adhesive layer containing peroxide as a whitening agent and a backing layer, the peroxide content decreases as time passes when the patch is stored at a temperature of 40° C. Accordingly, the whitening effect of the patch in vitro is also observed to be lower, compared to a new patch. For a gel type formulation, loss of peroxide over time is small even when excessive polymer is used as a film-forming agent and a peroxide stabilizer is not added. Even when the formulation has low peroxide stability, the desired effect can be obtained by using a small amount of chelating agent, such as EDTA or sodium citrate, known as a common peroxide stabilizer.

In a teeth whitening patch wherein the solvent of the gel layer is evaporated to form a sheet-shaped patch, when a stabilizer is not used in the composition, the peroxide stability is diminished, compared to the gel type formulation. It is also observed that the addition of a chelating agent results in a decrease in the peroxide stability of the patch, compared to a patch without a chelating agent. Furthermore, even when using Dequest phosphonates, which are known for their superior peroxide stabilizing effect, suitable peroxide stabilization cannot be obtained.

As described above, the reason why the peroxide stability in the patch differs in accordance with formulation type such as gel, liquid or sheet may be explained in a variety of ways. According to U.S. Pat. No. 4,320,102, peroxide is described as being readily decomposed through a reaction catalyzed by a minimal amount of metal contained in the composition. There have been reported data showing that the presence of 0.1 mg of iron, 0.2 mg of copper, 0.1 mg of magnesium or 0.02 mg of chromium per 1 l of peroxide will lead to decomposition of peroxide. A sheet-type patch formed by evaporation of the solvent in a solution-type or gel-type patch would include a high content of metal on the thin sheet of patch. Further, a sheet-type patch has a large surface area, which allows a high rate of reaction on the surface, and also lowers the stability of the peroxide.

The stabilizer used in the patch according to the present invention is mostly surfactant or emulsifier, which is believed to form micelles and produce a preferred effect on the peroxide stabilization of the product. In practice, it was found that when gel is applied thinly over a large surface area, the residual amount of peroxide decreases over time, while a gel of the same composition, contained in a container, is stable at a relatively high temperature.

However, according to the present invention, it is possible to solve the problem associated with peroxide stability in the patch at a high temperature, by using a dry type patch having multi-layer structure of three or more layers in which the layer containing peroxide is protected by the other layers In a dry type patch having a two-layer structure, the peroxide stability at a high temperature may be improved by using a glass polymer having good compatibility with peroxide in the adhesive layer and by using a peroxide stabilizer, when compared to the wet type patch. However, the dry type patch having multi-layer structure of three or more layers according to the present invention can achieve even better peroxide stability.

Further, the dry type patch according to the present invention may include a polyphosphate as an additional whitening agent along with peroxide in order to enhance the whitening effect.

Polyphosphates which can be used in the present invention include one or more selected from a group consisting of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP), acidic sodium metapolyphosphate and acidic sodium polyphosphate. In general, it is known that polyphosphate may be used effectively as a tartar controller in toothpaste to inhibit the formation of tartar or to remove tartar. Polyphosphate is also known as a good chelating agent to enhance the teeth whitening effect to some extent since it can effectively remove stains formed on the surface of the teeth, especially those formed of metal such as iron, calcium, magnesium, etc. derived from foods or working circumstances. It has been found that polyphosphate used along with peroxide in the patch according to the present invention may inhibit tartar formation and remove tartar by lengthening the contact time between teeth and polyphosphate. In practice, it is observed that when attaching the patch of the present invention to teeth, surface of teeth and gaps between teeth get cleaned.

Polymers which can be used in the backing layer of the patch according to the present invention include cellulose acetate phthalate, polyvinyl acetate, ethyl cellulose, polymethyl methacrylate, methacryloylethyl betain/methacrylate copolymer, commercially available under the trade name of Yukaformer manufactured by Mitsubishi, methacrylic acid copolymers such as Eudragit L 100, Eudragit L 125, Eudragit L 100-55, Eudragit L 30D-55, aminoalkylmethacrylate copolymers such as Eudragit E 100, Eudragit E 125, Eudragit RL 100, Eudragit RL 30D), or mixtures thereof. In addition, a polymer used as enteric coating material, which is not dissolved at pH 6 to 8 in oral cavity may be used.

In addition to the casting process using solvents, sheets of the patch may be manufactured by an extrusion process using thermoplastic polymers. Considering the efficiency of manufacturing process, a thin and flexible sheet, which is insoluble in water and impermeable to water, made of polyethylene (PE), ethylvinyl acetate (EVA), ethylvinyl alcohol, polyester or polyurethane is preferably used as the backing layer, since it is possible to omit the manufacturing process of the backing layer.

The backing layer may contain any plasticizer for the same reason in the contact adhesive layer and the active material reservoir layer. In this case, including the plasticizers described above, such as propylene glycol, glycerin, polyethylene glycol. Many kinds of plasticizer can be used depending on the solvent used. For example, castor oil or hydrogenated castor oil may also be used.

Further, upon attaching the patch of the present invention to teeth, in order to make the teeth visually white, any white pigment may be used in the backing layer. For example, titanium dioxide, talc, hydroxyapatite, zinc oxide, or mixtures thereof may be used as the white pigment. When these pigments are not compatible with peroxide used as whitening agent, surface-treated titanium dioxide may be used. In addition, it is possible to employ pearl material or pigments of a variety of colors depending on individual tastes.

In the teeth whitening patch, which is directly attached onto teeth in oral cavity, taste or flavor is a very important factor. Further, unlike toothpaste, it is removed some time after attachment to teeth, which lowers the fresh feeling with the lapse of time. On the other hand, the patch has the advantage that a specific flavor or taste lasts a long time since it may be attached for thirty minutes or longer at one time, unlike toothpaste normally used for one to three minutes. According to the present invention, flavor may be added to one or more layers of the contact adhesive layer, the active material reservoir layer and the backing layer. Preferably, the flavor is added to the active material reservoir layer containing peroxide so as to mask the taste of peroxide-containing layer and give flavor to the patch. It is also preferable for the flavor to be added to the water insoluble backing layer for a sustained faint fragrance.

In accordance with the present invention, such substances as enzymes, particularly dextranase or glucose oxidase, which cannot be used in conventional toothpaste due to their instability over time, may be used alone or in a mixture. It is also possible to add papain, which is known to have teeth whitening effect. Further, when applying the present invention for the treatment of oral disease, triclosan, chlorhexidine, vitamin E or its derivatives, such as, vitamin E acetate as well as oxidants, chlorophyll or its derivatives which are effective in removing foul breath may be added with the flavor.

It is known that staining due to tetracycline or smoking, or intrinsic staining requires more time to be whitened, compared to the staining due to food. Unlike familiar toothpaste, it is uncomfortable to attach and remove a teeth whitening patch for a long period of time. Accordingly, it is desirable to obtain a whitening effect in as short time period as possible. In order to shorten the time required for teeth whitening, a peroxide activator may be used along with peroxide. Since the stabilization of reactive peroxide in the patch is not easy, it is not preferable that a peroxide activator be added to the layer containing peroxide. However, the patch according to the present invention has a multi-layer structure of three or more layers so that the peroxide activator may be contained in other layers, such as the contact adhesive layer, rather than the active material reservoir layer containing peroxide. Of course, the present invention is not restricted to the addition of peroxide activator only to the contact adhesive layer.

Any substance known to activate peroxide may be used as the peroxide activator of the present invention. Metals such as Fe, Fe salts such as ferric chloride, Cu, Cu salts, Ca, Ca salts such as calcium hydroxide and calcium acetate, Mn, Mn salts, Pt, Pt salts, Pd, Pd salts, Ag, Ag salts, manganese gluconate, sodium bicarbonate, sodium hydroxide, activated charcoal and combinations thereof may be used as the peroxide activator.

In an embodiment of the patch formulation according to the present invention containing a peroxide activator in the contact adhesive layer, the contact adhesive layer contains substantially no peroxide and comprises a hydrophilic glass polymer as the primary polymer, thereby having little of no adhesive strength when in a pouch during storage. A barrier layer containing neither peroxide nor peroxide activator may be interposed between the contact adhesive layer and the active material reservoir layer. When hydrated by water upon attachment to the teeth, the patch has substantial adhesive strength along with the release of the peroxide activator, then a barrier layer containing neither peroxide nor peroxide activator is dissolved, and subsequently, an active material reservoir layer containing peroxide is dissolved to release peroxide, which meets with the peroxide activator to accelerate its whitening effect.

Preferred Embodiments

PREPARATION EXAMPLES

Example 1–28, Comparative Example 1–14

In accordance with the compositions described below, the respective patches of Examples 1–28 and Comparative Examples 1–14 are prepared. The layers are prepared using conventional extrusion or solvent casting processes. Each solution as indicated below is prepared and coated onto a suitable carrier substrate or casting drum to prepare layers by solvent casting. The solution is dried to form a film or layer. Preferably, the backing layer is cast initially, and the active material reservoir layer and adhesive layer are subsequently cast thereon in sequence. Abbreviations used below have the following meanings.

TKPP: tetrapotassium pyrophosphate
SAPP: sodium acid pyrophosphate
TSPP: tetrasodium pyrophosphate Example 1

| Solution for preparing contact adhesive layer | |
|---|---|
| Polyvinyl alcohol | 10% |
| Glycerin | 3% |
| Water | to 100% |

| Solution for preparing active material reservoir layer containing peroxide | |
|---|---|
| Polyvinyl pyrrolidone | 22% |
| Hydrogen peroxide | 5% |
| Glycerin | 10% |
| Ethanol | 30% |
| Water | to 100% |

| Solution for preparing backing layer | |
|---|---|
| Polyvinyl acetate | 5% |
| Glycerin | 5% |
| Ethanol | to 100% |

Example 2

| Solution for preparing contact adhesive layer | |
|---|---|
| Polyvinyl pyrrolidone | 5% |
| Hydroxypropylmethyl cellulose | 5% |
| Propylene glycol | 5% |
| l-menthol (flavor) | 1% |
| Ethanol | to 100% |

| Solution for preparing active material reservoir layer containing peroxide | |
|---|---|
| Polyethylene oxide | 6% |
| Polyvinyl pyrrolidone | 20% |
| Sodium percarbonate | 15% |
| Propylene glycol | 3% |
| Ethanol | to 100% |

| Solution for preparing backing layer | |
|---|---|
| Ethyl cellulose | 16% |
| Castor oil | 8% |
| Ethanol | to 100% |

Example 3

| Solution for preparing contact adhesive layer | |
|---|---|
| Polyquaternium-39 | 10% |
| Water | to 100% |

| Solution for preparing active material reservoir layer containing peroxide | |
|---|---|
| Polyethylene oxide | 15% |
| Carbamide peroxide | 10% |
| Methyl Salicylate (flavor) | 0.4% |
| Ethanol | 50% |
| Water | to 100% |
| Backing layer | |
| Polyethylene | |

Example 4

Solution for preparing contact adhesive layer

| | |
|---|---|
| Hydroxypropyl cellulose | 10% |
| Ethanol | to 100% |

Solution for preparing active material reservoir layer containing peroxide

| | |
|---|---|
| PVP/VA copolymer | 20% |
| Hydroxyethyl cellulose | 20% |
| Hydrogen peroxide | 3% |
| SAPP | 3% |
| Alkyldiphenyloxide disulphonate | 1% |
| Glycerin | 5% |
| Water | to 100% |

Solution for preparing backing layer

| | |
|---|---|
| Eudragit | 15% |
| Propylene glycol | 5% |
| Ethanol | to 100% |

Example 5

Solution for preparing contact adhesive layer

| | |
|---|---|
| Hydroxypropyl cellulose | 10% |
| Polyvinyl pyrrolidone | 5% |
| Ethanol | to 100% |

Solution for preparing active material reservoir layer containing peroxide

| | |
|---|---|
| Polyalkylvinyl ether-maleic acid copolymer | 12% |
| Polyvinyl alcohol | 5% |
| Tetrasodium pyrophosphate peroxidate | 6% |
| Sorbitan trioleate | 2% |
| Glycerin | 5% |
| NaOH | appropriate (pH up to 7) |
| Water | to 100% |

Solution for preparing backing layer

| | |
|---|---|
| Polymethylmethacrylate | 8% |
| Acetone | to 100% |

Example 6

Solution for preparing contact adhesive layer

| | |
|---|---|
| Polyalkylvinyl ether-maleic acid copolymer | 12% |
| Glycerin | 3% |
| Sodium bicarbonate | 5% |
| Water | to 100% |

Solution for preparing active material reservoir layer containing peroxide

| | |
|---|---|
| Polyvinyl pyrrolidone | 15% |
| Hydrogen peroxide | 1.5% |
| Glycerin | 5% |
| Sorbitan fatty acid ester | 3% |
| Water | to 100% |

Solution for preparing backing layer

| | |
|---|---|
| Ethyl cellulose | 20% |
| Eudragit | 5% |
| Castor oil | 12% |
| Mint (flavor) | 0.2% |
| Ethanol | to 100% |

Example 7

Solution for preparing contact adhesive layer

| | |
|---|---|
| Polyalkylvinyl ether-maleic acid copolymer | 12% |
| Glycerin | 3% |
| Sodium bicarbonate | 10% |
| Water | to 100% |

Solution for preparing active material reservoir layer containing peroxide

| | |
|---|---|
| Hydroxypropyl cellulose | 10% |
| Polyvinyl pyrrolidone | 10% |
| Hydrogen peroxide | 8% |
| SAPP | 1% |
| Glycerin | 5% |
| Sorbitan monolaurate | 1% |
| Water | to 100% |

Backing layer

Polyethylene

Example 8

Solution for preparing contact adhesive layer

| | |
|---|---|
| Polyethylene oxide | 10% |
| Glycerin | 5% |
| Calcium acetate | 0.1% |
| Water | to 100% |

Solution for preparing barrier layer

| | |
|---|---|
| Polyvinyl pyrrolidone | 35% |
| Hydroxypropylmethyl cellulose | 3% |
| Ethanol | to 100% |

Solution for preparing active material reservoir layer containing peroxide

| | |
|---|---|
| Polyquaternium | 10% |
| Polyvinyl pyrrolidone | 5% |
| Calcium percarbonate | 2% |
| Glycerin | 5% |
| Ethanol | to 100% |
| Backing layer | |
| Polyurethane | |

Example 9

Solution for preparing contact adhesive layer

| | |
|---|---|
| Carboxypolymethylene | 2% |
| Fe | 0.1% |
| Water | to 100% |

Solution for preparing barrier layer

| | |
|---|---|
| Hydroxypropylmethyl cellulose | 5% |
| Lemon Mint (flavor) | 0.3% |
| Ethanol | to 100% |

Solution for preparing active material reservoir layer containing peroxide

| | |
|---|---|
| Polyethylene oxide | 10% |
| Polyquaternium | 10% |
| Hydrogen peroxide | 5% |
| Propylene glycol | 7% |
| Ethanol | to 100% |

Solution for preparing backing layer

| | |
|---|---|
| Cellulose acetate phthalate | 30% |
| Castor oil | 6% |
| Mixture of acetone and ethanol (acetone: ethanol = 4:1) | to 100% |

Example 10

Solution for preparing contact adhesive layer

| | |
|---|---|
| Hydroxyethyl cellulose | 20% |
| Polyalkylvinyl ether-maleic acid copolymer | 5% |
| NaOH | appropriate (pH up to 8) |
| Water | to 100% |

Solution for preparing active material reservoir layer containing peroxide

| | |
|---|---|
| Polyquaternium | 10% |
| Polyvinyl pyrrolidone-vinyl acetate copolymer | 5% |
| Sodium percarbonate | 20% |
| Glycerin | 5% |
| Ethanol | to 100% |

Solution for preparing active material reservoir layer

| | |
|---|---|
| Polyvinyl alcohol | 35% |
| Dextranase | 0.1% |
| Glucose oxidase | 0.1% |
| Water | to 100% |

Solution for preparing backing layer

| | |
|---|---|
| Ethyl cellulose | 25% |
| Titanium dioxide | 2% |
| Yukaformer | 2% |
| Ethanol | to 100% |

Comparative Example 1

Solution for preparing adhesive layer containing active material

| | |
|---|---|
| Polyvinyl alcohol | 10% |
| PEG-ascorbic acid | 6% |
| Propylene glycol | 3.1% |
| Water | to 100 |

| Solution for preparing backing layer | |
| --- | --- |
| Ethyl cellulose | 10% |
| Castor oil | 4% |
| Ethanol | to 100 |

Comparative Example 2

| Solution for preparing adhesive layer containing active material | |
| --- | --- |
| Polyalkylvinyl ether-maleic acid copolymer | 20% |
| Tetrasodium pyrophosphate peroxidate | 6% |
| Dequest | 0.1% |
| Water | to 100% |

| Solution for preparing backing layer | |
| --- | --- |
| Polyvinyl acetate | 5% |
| Yukaformer | 5% |
| Glycerin | 6% |
| Ethanol | to 100% |

Comparative Example 3

| Solution for preparing adhesive layer containing active material | |
| --- | --- |
| Carboxypolymethylene | 12% |
| Hydrogen peroxide | 5.3% |
| Glycerin | 80% |
| Water | to 100% |
| Backing layer | |
| Polyethylene | |

Comparative Example 4

| Solution for preparing adhesive layer containing active material | |
| --- | --- |
| Shellac | 12% |
| Tetrasodium pyrophosphate peroxidate | 5% |
| NaOH | appropriate (pH up to 7) |
| Water | to 100% |

| Solution for preparing backing layer | |
| --- | --- |
| Polymethylmethacrylate | 8% |
| Acetone | to 100% |

Comparative Example 5

| Solution for preparing adhesive layer containing active material | |
| --- | --- |
| Polyalkylvinyl ether-maleic acid copolymer | 12% |
| Hydrogen peroxide | 3% |
| EDTA | 0.15% |
| NaOH | appropriate (pH up to 7) |
| Water | to 100% |

| Solution for preparing backing layer | |
| --- | --- |
| Ethyl cellulose | 10% |
| Castor oil | 6% |
| Ethanol | to 100% |

Test Examples

Test Example 1

The patches prepared as described above were measured for changes of surface condition after storing for one week at 40° C. The results are shown in Table 1, in which ○ means the condition with increased stickiness and discoloration; and X means the condition without increased stickiness and discoloration. Further, the adhesiveness of the patches after being attached to the teeth was also determined. In Table 1, +1 means good; 0 means fair; and −1 means poor.

TABLE 1

| | Increased Stickiness | Discoloration | Adhesiveness |
| --- | --- | --- | --- |
| Example 1 | X | X | +1 |
| Example 2 | X | X | +1 |
| Example 3 | X | X | +1 |
| Example 5 | X | X | +1 |
| Example 8 | X | X | +1 |
| Example 9 | X | X | +1 |
| Example 10 | X | X | +1 |
| Comparative Example 1 | ○ | ○ | −1 |
| Comparative Example 2 | X | X | +1 |
| Comparative Example 3 | X | X | −1 |
| Comparative Example 4 | ○ | X | 0 |
| Comparative Example 5 | X | X | +1 |

As seen in Table 1, the dry type patch having a multi-layer structure of three or more layers as in Examples 1, 2, 3, 5, 8, 9 and 10 or the dry type patch having double layers as in Comparative Examples 2 and 5, which contain the hydrophilic glass polymers in the adhesive layer, did not show increased stickiness and discoloration after being stored for one week at a temperature of 40° C. On the other hand, the dry type patch of two-layer structure as in Comparative Example 1, which contains polyvinyl alcohol as a hydrophilic glass polymer in the adhesive layer and uses ascorbic acid or derivatives thereof such as PEG-ascorbic acid as a whitening agent, showed increased stickiness and severe discoloration with the lapse of time. Further, the dry type patch having a two-layer structure as in Comparative Example 4, which uses shellac which has good compatibility with peroxide in the active material reservoir layer containing peroxide, showed increased stickiness. The wet type patch of Comparative Example 3, in which the adhesive layer is a gel, showed poor adhesive strength such that it detached from the teeth when the user coughed or spoke loudly, even though showing a good condition after being stored.

Test Example 2

Teeth whitening effect of the patches prepared above were measured according to the following method.

(1) Preparation of Contaminated Hydroxyapatite (HAP) Tablet Specimen

Hydroxyapatite powder was formed into a tablet by means of IR press. The resulting tablet was sintered at a temperature of 1000° C., molded by epoxy resin and etched using a strong acid. The tablet specimen was dipped in TSB (trypticase soybroth) solution having tea, coffee, iron and mucin dissolved therein and dried. Such contamination was repeated several times over one week. After the contamination, the specimen was washed under running water with a mild brushing to remove loose contaminants. Finally, the specimen was dried at room temperature.

(2) Evaluation of Teeth Whitening Effect

Initial luminosity values, L (100 indicates white and 0 indicates black) of the respective specimens were measured by means of chromoscope. The teeth whitening patches prepared in the above Preparation Examples were attached to the specimens which had been soaked in water. The specimens with the attached patches were stored in a thermohydrostat which had been set to conditions similar to those in an oral cavity, that is, at a temperature of 37° C. and a humidity of 95%. After a pre-determined time, the patches were detached from specimens. The detached specimens were washed with running water with a mild brushing and dried at room temperature. L value of each specimen was measured. Difference of L values before and after attaching the patches ΔL was calculated for each patch. The results are shown in Table 2.

TABLE 2

|  | ΔL (1 hour) | ΔL (3 hours) |
| --- | --- | --- |
| Example 4 | 33.45 ± 1.65 | 37.99 ± 0.31 |
| Example 5 | 28.99 ± 0.04 | 36.84 ± 1.15 |
| Example 6 | 40.15 ± 2.31 | 42.00 ± 2.00 |
| Comparative Example 1 | 7.05 ± 1.71 | 15.26 ± 2.37 |
| Comparative Example 3 | 14.55 ± 2.41 | 30.35 ± 3.24 |
| Comparative Example 5 | 14.73 ± 4.11 | 32.25 ± 3.33 |

As seen in Table 2, the patches of Examples 4 and 5 comprising peroxide along with polyphosphate as a whitening agent showed improved teeth whitening effect, when compared to those of Comparative Examples 1, 3 and 5 comprising peroxide alone. Further, the patch of Example 6 having four layers which contains a peroxide activator in the contact adhesive layer and peroxide in the active material reservoir layer showed prompt teeth whitening effect, compared to those containing no peroxide activator.

Test Example 3

Determination of Residue on Skin

The amount of residue on the skin after detaching the attached patches was determined by using a peel-off tester as follows: Each patch was weighed and attached onto the adhesion surface of a peel-off tester. After being detached mechanically, each patch was weighed and the amount of residue on the skin was calculated according to the following calculation: (the weight of patch before attachment—the weight of patch after peel-off)/(the weight of patch before attachment)×100 (%). The results are shown in Table 3.

TABLE 3

|  | Amount of residue on skin |
| --- | --- |
| Example 3 | 0% |
| Example 5 | 0% |
| Example 6 | 0% |
| Example 7 | 0% |
| Comparative Example 1 | 0% |
| Comparative Example 3 | 84% |
| Comparative Example 5 | 0% |

As shown in Table 3, the dry type patches having a two-layer or multi-layer structure of three or more layers had little or no amount of residue on the skin. On the other hand, the wet type patch of Comparative Example 3, in which the adhesive layer is gel, showed extremely high amount of residue on skins even though glass polymers were used.

Test Example 4

In the teeth whitening patches prepared according to the Preparation Examples, peroxide stability was evaluated after being stored in a pouch at the temperature of 40° C.

Evaluation of Peroxide Content in Patches

A solvent mixture which is capable of dissolving all layers of the patches was placed in an Erlenmeyer flask. An appropriate amount of the respective patches were weighed precisely, put into the flask and dissolved completely in the solvent mixture. 5 ml of 6 N HCl was added to the flask and about 2 g of potassium iodide was then dissolved in the solvent. The flask was kept for 1 hour in a cool and dark place. Then, the solution was titrated using 50 mM sodium thiosulphate and the peroxide content of the respective patches was quantified. The results are shown in Table 4.

TABLE 4

| Residual peroxide (%) | After 4 weeks | After 8 weeks | After 12 weeks |
| --- | --- | --- | --- |
| Example 4 | 82% | 83% | 79% |
| Example 7 | 89% | 85% | 80% |
| Comparative Example 2 | 80% | 73% | 50% |
| Comparative Example 3 | 82% | 60% | 41% |
| Comparative Example 5 | 78% | 67% | 55% |

As shown in Table 4, the dry type patches of Examples 4 or 7 using alkyldiphenyloxide disulphonate or sorbitan monolaurate as peroxide stabilizer showed improved effect on the stabilization of peroxide in the teeth whitening patches, when compared to those of Comparative Examples 2 or 5 using EDTA or Dequest.

Example 11

Adhesive layer preparation solution

| | |
|---|---|
| Polyvinyl alcohol | 10% |
| Glycerin | 3% |
| Water | to 100% |

Active material reservoir layer preparation solution

| | |
|---|---|
| Polyvinyl alcohol | 10% |
| Polyvinyl pyrrolidone | 3% |
| Tetrasodium pyrophosphate peroxidate | 5% |
| Alkyl aryl sulphonate (SLS) | 2% |
| Glycerin | 3% |
| Water | to 100% |

Backing layer preparation solution

| | |
|---|---|
| Ethyl cellulose | 8% |
| Eudragit | 5% |
| Castor oil | 4% |
| Ethanol | to 100% |

Example 12

Adhesive layer preparation solution

| | |
|---|---|
| Polyvinyl alcohol | 12% |
| Water | to 100% |

Active material reservoir layer preparation solution

| | |
|---|---|
| Polyvinyl pyrrolidone | 10% |
| Hydrogen peroxide | 5% |
| Glycerin | 10% |
| Ethanol | 30% |
| Water | to 100% |

Backing layer preparation solution

| | |
|---|---|
| Polyvinyl acetate | 5% |
| Yukaformer (Mitsubishi) | 5% |
| Glycerin | 6% |
| Ethanol | to 100% |

Example 13

Adhesive layer preparation solution

| | |
|---|---|
| Polyquaternium-39 | 10% |
| Water | to 100% |

Active material reservoir layer preparation solution

| | |
|---|---|
| Polyquaternium-39 | 10% |
| Carbamide peroxide | 10% |
| Ethanol | 50% |
| Water | to 100% |

Backing layer preparation solution

| | |
|---|---|
| Cellulose acetate phthalate | 30% |
| Castor oil | 4% |
| Mixture of acetone and ethanol (acetone:ethanol = 4:1) | to 100% |

Example 14

Adhesive layer preparation solution

| | |
|---|---|
| Polyalkyl vinyl ether-maleic acid copolymer (Grantrez S 97) | 12% |
| water | to 100% |

Active material reservoir layer preparation solution

| | |
|---|---|
| Ethyl cellulose | 12% |
| Hydrogen peroxide | 3% |
| Ethanol | to 100% |

Backing layer preparation solution

| | |
|---|---|
| Ethyl cellulose | 10% |
| Castor oil | 6% |
| Ethanol | to 100% |

Example 15

Adhesive layer preparation solution

| | |
|---|---|
| Polyvinyl pyrrolidone | 10% |
| Ethanol | to 100% |

Active material reservoir layer preparation solution

| | |
|---|---|
| Polyalkyl vinyl ether-maleic acid copolymer (Grantrez S 97) | 12% |
| Tetrasodium pyrophosphate peroxidate | 6% |
| Alkyl aryl sulphonate (SLS) | 10% |
| NaOH | appropriate (pH to 7) |
| Water | to 100% |

Backing layer preparation solution

| | |
|---|---|
| Ethyl cellulose | 10% |
| Castor oil | 6% |
| Ethanol | to 100% |

Example 16

Adhesive layer preparation solution

| | |
|---|---|
| Polyvinyl pyrrolidone-vinyl acetate copolymer | 10% |
| Water | to 100% |

Active material reservoir layer preparation solution

| | |
|---|---|
| Shellac | 12% |
| Tetrasodium pyrophosphate peroxidate | 5% |
| NaOH | appropriate (pH to 7) |
| Water | to 100% |

Backing layer preparation solution

| | |
|---|---|
| Polymethyl methacrylate | 8% |
| Acetone | to 100% |

Example 17

Adhesive layer preparation solution

| | |
|---|---|
| Polyquaternium-11 | 20% |
| Water | to 100% |

Active material reservoir layer preparation solution

| | |
|---|---|
| Shellac | 12% |
| Hydrogen peroxide | 1.5% |
| Ethanol | to 100% |

Backing layer preparation solution

| | |
|---|---|
| Eudragit | 15% |
| Propylene glycol | 5% |
| Ethanol | to 100% |

Example 18

Adhesive layer preparation solution

| | |
|---|---|
| Hydroxy propyl cellulose | 10% |
| Water | to 100% |

Active material reservoir layer preparation solution

| | |
|---|---|
| Polyvinyl pyrrolidone | 10% |
| Hydrogen peroxides | 1.5% |
| SAPP | 2% |
| Alkyl diphenyl oxide disulphonate | 1% |
| Glycerin | 5% |
| Water | to 100% |

Backing layer preparation solution

| | |
|---|---|
| Ethyl cellulose | 12% |
| Castor oil | 6% |
| Ethanol | to 100% |

Example 19

Adhesive layer preparation solution

| | |
|---|---|
| Polyvinyl alcohol | 12% |
| Water | to 100% |

Active material reservoir layer preparation solution

| | |
|---|---|
| Polyvinyl alcohol | 12% |
| Hydrogen peroxide | 1.5% |
| TSPP | 3.4% |
| Span 60 | 5% |
| Propylene glycol | 3% |
| Water | to 100% |

Backing layer preparation solution

| | |
|---|---|
| Ethyl cellulose | 8% |
| Cellulose acetate phthalate | 2% |
| Mixture of acetone and ethanol (acetone:ethanol = 4:1) | to 100% |

Example 20

Adhesive layer preparation solution

| | |
|---|---|
| Carbomer | 6% |
| NaOH | appropriate (pH to 7) |
| Water | to 100% |

Active material reservoir layer preparation solution

| | |
|---|---|
| Polyvinyl pyrrolidon | 18% |
| Hydrogen peroxide | 1.5% |
| Ethanol | to 100% |

Backing layer preparation solution

| | |
|---|---|
| Ethyl cellulose | 10% |
| Eudragit | 2% |
| Castor oil | 7% |
| Ethanol | to 100% |

Comparative Example 6

Adhesive layer preparation solution

| | |
|---|---|
| Polyvinyl alcohol | 10% |
| PEG-ascorbic acid | 6% |
| Propylene glycol | 3.1% |
| Water | to 100 |

Backing layer preparation solution

| | |
|---|---|
| Ethyl cellulose | 10% |
| Castor oil | 4% |
| Ethanol | to 100 |

Comparative Example 7

Adhesive layer preparation solution

| | |
|---|---|
| Polyalkyl vinyl ether-maleic acid copolymer (Grantrez S 97) | 12% |
| Tetrasodium pyrophosphate peroxidate | 6% |
| Dequest | 0.1% |
| Water | to 100% |

Backing layer preparation solution

| | |
|---|---|
| Polyvinyl acetate | 5% |
| Yukaformer | 5% |
| Glycerin | 6% |
| Ethanol | to 100% |

Comparative Example 8

Adhesive layer preparation solution

| | |
|---|---|
| Polyalkyl vinyl ether-maleic acid copolymer (Grantrez S 97) | 12% |
| Tetrasodium pyrophosphate peroxidate | 6% |
| EDTA | 0.15% |
| NaOH | appropriate (pH to 7) |
| Water | to 100% |

Backing layer preparation solution

| | |
|---|---|
| Ethyl cellulose | 10% |
| Castor oil | 6% |
| Ethanol | to 100 |

Comparative Example 9

| Adhesive layer preparation solution | |
| --- | --- |
| Carbopol | 12% |
| Hydrogen peroxide | 4.5% |
| SAPP | 0.48% |
| Glycerin | 80% |
| Water | to 100% |
| Backing layer | |
| Polyethylene strip | |

Comparative Example 10

| Adhesive layer preparation gel | |
| --- | --- |
| Shellac | 12% |
| Tetrasodium pyrophosphate peroxidate | 5% |
| NaOH | appropriate (pH to 7) |
| Water | to 100% |

| Backing layer preparation solution | |
| --- | --- |
| Poly methylmethacrylate | 8% |
| Acetone | to 100% |

Comparative Example 11

| Adhesive layer preparation | |
| --- | --- |
| Polyvinyl pyrrolidone | 10% |
| Hydrogen peroxide | 5% |
| Glycerin | 10% |
| Ethanol | 30% |
| Water | to 100% |

| Backing layer preparation solution | |
| --- | --- |
| Polyvinyl acetate | 5% |
| Yukaformer | 5% |
| Glycerin | 6% |
| Ethanol | to 100% |

Test Examples

Test Example 5

After storing patches prepared as described above for one week at 40° C., the patches were measured for changes of surface condition. They are graded on the following criteria: ○, increased in stickiness or discolored; X, not increased in stickiness nor discolored. Also, the adhesion of the patches after attached to the teeth is determined on the following criteria: +1: good; 0: fair; and −1: poor and the peel-off property is determined on the following criteria: +1: good; 0: fair; and −1: poor.

TABLE 5

| | Stickiness | Discoloration | Adhesion | Peel-off property |
| --- | --- | --- | --- | --- |
| Example 11 | X | X | +1 | +1 |
| Example 12 | X | X | +1 | +1 |
| Example 13 | X | X | +1 | +1 |
| Example 15 | X | X | +1 | +1 |
| Example 17 | X | X | +1 | +1 |
| Example 18 | X | X | +1 | +1 |
| Example 19 | X | X | +1 | +1 |
| Example 20 | X | X | +1 | +1 |
| Comparative Example 5 | ○ | ○ | −1 | +1 |
| Comparative Example 10 | ○ | ○ | 0 | 0 |
| Comparative Example 11 | X | X | +1 | 0 |

As seen in Table 5, Examples wherein the hydrophilic glass polymers used in the contact adhesive layer of the patch of the three-layer structure according to the present invention did not show an increase in stickiness and changes of color after being stored for one week at a temperature of 40° C. However, Comparative Examples wherein polyvinyl alcohol, which is a hydrophilic glass polymer, was used in the adhesive layer of the patch of a two-layer structure, and instead of a peroxide, ascorbic acid or a derivative thereof such as PET-ascorbic acid were used as a whitening agent, showed an increase in stickiness and severe discoloration as time passed. Further, Example 16, wherein shellac, which is highly compatible with peroxide, was used in the contact adhesive layer, the patch did not show an increase in stickiness because it has a three-layer structure. However, Comparative Example 10 which has a two-layer structure and uses shellac (because the melting point of shellac is about 37° C.) showed an increase in stickiness after being stored. In addition, upon comparison between Example 12 and Comparative Example 11, it can be seen that the two-layer patch showed good adhesion strength but poor peel-off property, while the three-layer patch further comprising a contact adhesive layer formed of PVA according to the present invention is excellent in both adhesion strength and peel-off property.

Test Example 6

The tooth whitening effect of patches of Examples 11, 16, 19 and 20 and Comparative Examples 6, 9 and 10 were measured according to the same method used in Test Example 2.

The results are shown in Table 6.

TABLE 6

| | ΔL (1 hour) | ΔL (3 hours) |
| --- | --- | --- |
| Example 11 | 33.45 ± 3.25 | 38.95 ± 5.31 |
| Example 16 | 34.55 ± 4.55 | 39.23 ± 3.77 |
| Example 18 | 32.38 ± 3.44 | 40.00 ± 3.88 |
| Example 19 | 37.10 ± 3.44 | 38.00 ± 3.88 |
| Example 20 | 14.73 ± 4.11 | 32.25 ± 3.33 |
| Comparative Example 6 | 7.05 ± 1.71 | 15.26 ± 2.37 |
| Comparative Example 9 | 14.55 ± 2.41 | 30.35 ± 3.24 |
| Comparative Example 10 | 17.98 ± 3.05 | 20.05 ± 2.99 |

As seen in Table 6, patches comprising peroxide as a whitening agent were superior in tooth whitening effect, when compared to patches comprising an ascorbic acid or derivatives thereof. Also, it was noted that patches comprising peroxide in combination with a polyphosphate or an addition compound of peroxide and a pyrophosphate as a tooth whitening agent exhibit improved tooth whitening effect compared to patches comprising peroxide only.

Test Example 7

The teeth whitening patches prepared in accordance with the composition described in Examples 13, 14, 15 and 17 and Comparative Examples 7, 8 and 9 were evaluated for their stability over time according to the same method set forth in Test Example 4.

The results are shown in Table 7.

TABLE 7

| Residual peroxide | Ex. 13 | Ex. 14 | Ex. 15 | Ex. 17 | Comp. Ex. 7 | Comp. Ex. 8 | Comp. Ex. 9 |
|---|---|---|---|---|---|---|---|
| 1 week | 98% | 100% | 98% | 100% | 80% | 86% | 96% |
| 2 week | 94% | 100% | 95% | 100% | 65% | 70% | 91% |
| 4 week | 90% | 98% | 94% | 100% | 50% | 61% | 84% |
| 6 week | 88% | 96% | 92% | 97% | 42% | 50% | 71% |
| 8 week | 87% | 94% | 88% | 93% | 16% | 30% | 65% |

As shown from the results of Examples 14 and 15 and Comparative Examples 7 and 8 in table 7, adding a peroxide stabilizer and constructing the patch in the three-layer structure improves stability over time when other compositional components are the same. However, in the case of Examples 13 and 20 which did not include a stabilizer for peroxide, since the glass polymer and peroxide are highly compatible with each other, the stability over time of peroxide at a high temperature could be achieved only by adjusting the ratio of water and ethanol in the adhesive layer during the production process. Comparative Example 9 is a wet type whitening agent patch. It was observed that residual peroxide content in the patch reduced rapidly after 4 weeks.

Example 21

| Solution for preparing contact adhesive layer | |
|---|---|
| Polyalkylvinyl ether-maleic acid copolymer | 12% |
| TKPP | 2% |
| Sodium Bicarbonate | 5% |
| Glycerin | 3% |
| Water | to 100% |

| Solution for preparing barrier layer | |
|---|---|
| Polyvinyl alcohol | 10% |
| Water | to 100% |

| Solution for preparing active material reservoir layer containing peroxide | |
|---|---|
| Polyvinyl pyrrolidone | 15% |
| Hydrogen peroxide | 1.5% |
| Sorbitan monooleate(Span80) | 2% |
| Glycerin | 3% |
| Water | to 100% |

| Solution for preparing backing layer | |
|---|---|
| Ethyl cellulose | 8% |
| Eudragit | 5% |
| Caster Oil | 4% |
| Ethanol | to 100% |

Example 22

| Solution for preparing contact adhesive layer | |
|---|---|
| Hydroxypropyl cellulose | 12% |
| Glycerin | 3% |
| Sodium bicarbonate | 5% |
| Water | to 100% |

| Solution for preparing barrier layer | |
|---|---|
| Polyalkylvinyl ether-maleic acid copolymer | 12% |
| Propylene glycol | 3% |
| Water | to 100% |

| Solution for preparing active material reservoir layer containing peroxide | |
|---|---|
| Polyquaternium 39 | 10% |
| Hydrogen Peroxide | 1.5% |
| SAPP | 2% |
| Sorbitan monolaurate (Span 20) | 2% |
| Water | to 100% |

| Solution for preparing backing layer | |
|---|---|
| Ethyl cellulose | 12% |
| Castor oil | 6% |
| Ethanol | to 100% |

Example 23

| Solution for preparing contact adhesive layer | |
|---|---|
| Polyalkylvinyl ether-maleic acid copolymer | 12% |
| Glycerin | 3% |
| Calcium acetate | 0.1% |
| NaOH | pH up to 7 |
| Water | to 100% |

| Solution for preparing barrier layer | |
|---|---|
| Polyvinyl alcohol | 10% |
| Water | to 100% |

| Solution for preparing active material reservoir layer containing peroxide | |
|---|---|
| Polyvinyl pyrrolidone | 15% |
| Hydrogen peroxide | 1.5% |
| Glycerin | 3% |
| Sorbitan monooleate | 2% |
| Water | to 100% |

| Solution for preparing backing layer | |
|---|---|
| Ethyl cellulose | 8% |
| Eudragit | 5% |
| Caster Oil | 4% |
| Ethanol | to 100% |

Example 24

| Solution for preparing contact adhesive layer | |
|---|---|
| Polyalkylvinyl ether-maleic acid copolymer | 12% |
| Calcium hydroxide | pH up to 7 |
| Glycerin | 3% |
| Water | to 100% |

| Solution for preparing barrier layer | |
|---|---|
| PVP/VA copolymer | 10% |
| Water | to 100% |

| Solution for preparing active material reservoir layer containing peroxide | |
|---|---|
| Polyquaternium 39 | 10% |
| Calcium peroxide | 10% |
| Ethanol | 50% |
| Water | to 100% |

| Solution for preparing backing layer | |
|---|---|
| Polyvinyl acetate | 5% |
| Methacryloylethyl betain/methacrylate copolymer (Yukaformer) | 5% |
| Glycerin | 6% |
| Ethanol | to 100% |

Example 25

| Solution for preparing contact adhesive layer | |
|---|---|
| Hydroxypropyl cellulose | 20% |
| NaOH | pH up to 8 |
| Water | to 100% |

| Solution for preparing barrier layer | |
|---|---|
| Polyvinyl pyrrolidone | 16% |
| Ethanol | to 100% |

| Solution for preparing active material reservoir layer containing peroxide | |
|---|---|
| Polyalkylvinyl ether-maleic acid copolymer | 12% |
| Tetrasodium pyrophosphate peroxidate | 6% |
| Alkylaryl sulphonate | 10% |
| NaOH | pH up to 7 |
| Water | to 100% |

| Solution for preparing backing layer | |
|---|---|
| Ethyl cellulose | 10% |
| Caster oil | 6% |
| Ethanol | to 100% |

Example 26

| Solution for preparing contact adhesive layer | |
|---|---|
| Polyquaternium 39 | 10% |
| TSPP | 3% |
| $Fe^{2+}$ | 50 ppm |
| Water | to 100% |

| Solution for preparing barrier layer | |
|---|---|
| Hydroxypropyl methyl cellulose | 2% |
| Water | to 100% |

| Solution for preparing active material reservoir layer containing peroxide | |
|---|---|
| Polyquaternium 39 | 10% |
| Hydrogen peroxide | 2% |
| Ethanol | 50% |
| Water | to 100% |

| Solution for preparing backing layer | |
|---|---|
| Cellulose acetate phthalate | 30% |
| Castor oil | 4% |
| Acetone:Ethanol = 4:1 | to 100% |

Example 27

| Solution for preparing contact adhesive layer | |
|---|---|
| Polyalkylvinyl ether-maleic acid copolymer | 12% |
| NaOH | pH up to 9 |
| Water | to 100% |

| Solution for preparing barrier layer | |
|---|---|
| Polyvinyl alcohol | 10% |
| Water | to 100% |

| Solution for preparing active material reservoir layer containing peroxide | |
|---|---|
| Polyvinyl pyrrolidone | 10% |
| Hydrogen peroxide | 1.5% |
| SAPP | 2% |
| Alkyldiphenyloxide disulphonate | 1% |
| Glycerin | 5% |
| Water | to 100% |

| Solution for preparing backing layer | |
|---|---|
| Ethyl cellulose | 12% |
| Caster oil | 6% |
| Ethanol | to 100% |

Example 28

| Solution for preparing contact adhesive layer | |
|---|---|
| Carboxypolymethylene (Carbomer) | 6% |
| NaOH | pH up to 7 |
| Water | to 100% |

| Solution for preparing barrier layer | |
|---|---|
| Polyvinyl alcohol | 10% |
| Water | to 100% |

| Solution for preparing active material reservoir layer containing peroxide | |
|---|---|
| Polyvinyl pyrrolidone | 18% |
| Hydrogen peroxide | 1.5% |
| Ethanol | to 100% |

| Solution for preparing backing layer | |
|---|---|
| Ethyl cellulose | 10% |
| Eudragit | 2% |
| Caster oil | 7% |
| Ethanol | to 100% |

Comparative Example 12

| Solution for preparing contact adhesive layer | |
|---|---|
| Polyalkylvinyl ether-maleic acid copolymer | 12% |
| Glycerin | 3% |
| Water | to 100% |

| Solution for preparing active material reservoir layer containing peroxide | |
|---|---|
| Polyvinyl pyrrolidone | 15% |
| Hydrogen peroxide | 1.5% |
| TKPP | 2% |
| Sorbitan monooleate (Span80) | 2% |
| Glycerin | 3% |
| Water | to 100 |

| Solution for preparing backing layer | |
|---|---|
| Ethyl cellulose | 8% |
| Eudragit | 5% |
| Caster Oil | 4% |
| Ethanol | to 100% |

Comparative Example 13

| Solution for preparing adhesive layer containing peroxide | |
|---|---|
| Polyalkylvinyl ether-maleic acid copolymer | 12% |
| Hydrogen peroxide | 1.5% |
| TKPP | 2% |
| Sorbitan monooleate (Span80) | 2% |
| Glycerin | 3% |
| Water | to 100% |

| Solution for preparing backing layer | |
|---|---|
| Ethyl cellulose | 8% |
| Eudragit | 5% |
| Caster Oil | 4% |
| Ethanol | to 100% |

Comparative Example 14

| Solution for preparing adhesive layer containing peroxide | |
|---|---|
| Polyalkylvinyl ether-maleic acid copolymer | 12% |
| Tetrasodium pyrophosphate peroxidate | 6% |
| EDTA | 0.15% |
| NaOH | pH up to 7 |
| Glycerin | 3% |
| Water | to 100% |

| Solution for preparing backing layer | |
|---|---|
| Ethyl cellulose | 10% |
| Caster Oil | 6% |
| Ethanol | to 100% |

Comparative Example 15

| Solution for preparing adhesive layer containing peroxide | |
|---|---|
| Carbopol | 12% |
| Hydrogen peroxide | 4.5% |
| SAPP | 0.48% |
| Glycerin | 80% |
| Water | to 100% |
| Backing layer | |
| Polyethylene | |

Test Examples

Test Example 8

The tooth whitening effect of patches of Examples 21, 22 and 28 and Comparative Examples 12, 13 14 and 15 were measured according to the same method used in Test Example 2.

The results are shown in Table 8 and 9.

TABLE 8

| | ΔL (1 hour) | ΔL (3 hours) |
|---|---|---|
| Example 21 | 40.27 ± 0.31 | 42.95 ± 0.05 |
| Example 22 | 39.23 ± 3.77 | 41.15 ± 2.11 |
| Example 28 | 30.25 ± 3.00 | 32.30 ± 1.50 |
| Comparative Example 12 | 33.45 ± 3.25 | 40.70 ± 0.95 |
| Comparative Example 13 | 32.35 ± 1.38 | 38.75 ± 0.51 |
| Comparative Example 14 | 34.88 ± 1.54 | 40.00 ± 3.24 |
| Comparative Example 15 | 17.98 ± 5.05 | 30.35 ± 3.24 |

TABLE 9

| | ΔL (10 min) | ΔL (30 min) | ΔL (45 min) | ΔL (60 min) |
|---|---|---|---|---|
| Example 21 | 25.96 ± 1.65 | 33.45 ± 3.25 | 36.05 ± 2.51 | 40.27 ± 0.31 |
| Example 22 | 26.00 ± 0.39 | 34.55 ± 4.55 | 35.62 ± 4.24 | 39.23 ± 3.77 |
| Example 28 | 13.45 ± 4.11 | 19.73 ± 2.36 | 25.87 ± 3.33 | 30.23 ± 3.00 |
| Comparative Example 12 | 15.05 ± 1.31 | 23.26 ± 2.01 | 28.00 ± 1.99 | 33.45 ± 3.25 |
| Comparative Example 13 | 14.55 ± 2.41 | 24.35 ± 3.24 | 30.35 ± 3.10 | 32.35 ± 1.38 |
| Comparative Example 14 | 15.33 ± 0.87 | 25.67 ± 1.27 | 30.90 ± 3.34 | 34.88 ± 1.54 |
| Comparative Example 15 | 7.98 ± 3.21 | 14.98 ± 2.02 | 15.21 ± 1.27 | 17.98 ± 3.05 |

As seen in Tables 8 and 9, the patches of Examples 21 and 22 comprising peroxide along with polyphosphate as a whitening agent showed improved teeth whitening effect, compared to those of Examples 28 comprising peroxide alone. Further, the patches of Example 21, 22, and 28 having four layers which contain an activator for peroxide in the contact adhesive layer and peroxide in the active material reservoir layer showed prompt teeth whitening effect, when compared to those containing no activator for peroxide.

Test Example 9

Determination of Residue on Skin

The amount of residue on skins after detaching the patches of Examples 23, 25, 26 and 27 and Comparative Example 15 was determined according to the same method used in Test Example 3.

The results are shown in Table 10.

TABLE 10

| | Amount of residue on skins |
|---|---|
| Example 23 | 0% |
| Example 25 | 0% |
| Example 26 | 0% |
| Example 27 | 0% |
| Comparative Example 15 | 84% |

As shown in Table 10, the dry type patches having multi-layer structure had no or little amount of residue on skin. On the other hand, the wet type patch of Comparative Example 24 in which the adhesive layer is a gel, even though using glass polymers, showed an extremely high amount of residue on the skin.

Test Example 10

The teeth whitening patches prepared in accordance with the composition described in Examples 21 and 25 and Comparative Examples 12, 13 14 and 15 were evaluated for their stability over time according to the same method set forth in Test Example 4.

The results are shown in Table 11 and 12.

TABLE 11

| Residual peroxide (%) | After 4 weeks | After 8 weeks | After 12 weeks |
|---|---|---|---|
| Example 21 | 94% | 88% | 84% |
| Example 25 | 86% | 80% | 76% |
| Comparative Example 12 | 94% | 88% | 80% |
| Comparative Example 13 | 82% | 75% | 60% |
| Comparative Example 14 | 61% | 30% | 14% |
| Comparative Example 15 | 84% | 65% | 41% |

TABLE 12

| Residual Peroxide | Example 21 | Example 25 | Comparative Example 12 | Comparative Example 13 | Comparative Example 14 | Comparative Example 15 |
|---|---|---|---|---|---|---|
| 1 week | 98% | 92% | 98% | 95% | 89% | 96% |
| 2 week | 95% | 88% | 95% | 85% | 70% | 91% |
| 4 week | 94% | 86% | 94% | 82% | 61% | 84% |
| 6 week | 92% | 83% | 92% | 80% | 50% | 71% |
| 8 week | 88% | 80% | 88% | 75% | 30% | 65% |

As shown in Tables 11 and 12, the dry type patches of Examples 21 or 25 using sorbitan monooleate or alkylaryl sulphonate as peroxide stabilizer showed improved peroxide stabilization compared to those of Comparative Example 14 or 15 using EDTA or not using peroxide stabilizer.

INDUSTRIAL APPLICABILITY

As is apparent from the above description, the dry type patches for teeth whitening having a multi-layer structure of three or more layers including a contact adhesive layer, an active material reservoir layer containing peroxide and a backing layer according to the present invention have superior teeth whitening effect. Further, the patches are excellent in their adhesiveness and peel-off property, thereby being convenient to use. In addition, the peroxide-containing layer of the dry type patches according to the present invention does not stick to the hands or face during its attachment to the teeth. Furthermore, the peroxide-containing layer is covered and protected by other layers, which makes it safe to the human body. Especially, the patches of the present invention show an excellent peroxide stability in the patch at a high temperature.

What is claimed is:

1. A dry patch for whitening teeth having a multi-layer structure of three or more layers comprising a contact adhesive layer, a backing layer, and an active material reservoir layer comprising a peroxide, a peroxide stabilizer, and a hydrophilic glass polymer which is positioned between the contact adhesive layer and the backing layer;
   wherein the contact adhesive layer is substantially free of peroxide and comprises a hydrophilic glass polymer as a base polymer; and wherein the contact adhesive layer provides substantial adhesive attachment to the teeth when hydrated by water and placed in contact with the teeth and has insubstantial adhesiveness before hydration and attachment to the teeth,
   and the active material reservoir layer releases peroxide contained therein subsequent to the hydration and attachment of the contact adhesive layer to the teeth.

2. The patch for whitening teeth of claim 1, wherein the peroxide contained in the active material reservoir layer is selected from the group consisting of hydrogen peroxide, carbamide peroxide, calcium peroxide, sodium percarbonate, sodium perborate, tetrasodium pyrophosphate peroxidate and combinations thereof.

3. The patch for whitening teeth of claim 1, wherein the hydrophilic glass polymer is selected from the group consisting of polyalkylvinyl ether-maleic acid copolymer, polyvinyl alcohol, polyacrylic acid, Poloxamer 407, polyvinyl pyrrolidone-vinyl acetate copolymer, polyethylene oxide, polyvinyl pyrrolidone, Polyquaterium-11, Polyquaterium-39, carboxypolymethylene, hydroxypropylmethyl cellulose, hydroxyethyl cellulose, hydroxypropyl cellulose, gelatin, sodium alginate and combinations thereof.

4. The patch for whitening teeth of claim 1, wherein the peroxide stabilizer contained in the active material reservoir layer is selected from the group consisting of an alkylaryl sulphonate, an alkyl sulphonate, an alkyl carboxylate, an alkyldiphenyloxide disulphonate, sorbitan monolaurate, sorbitan monopalmitate, sorbitan monostearate, sorbitan monooleate, sorbitan trioleate, a POE sorbitan fatty acid ester, a glycerin fatty acid ester, an organic acid monoglyceride, a sodium stearyl lactate, a polysorbate and combinations thereof.

5. The patch for whitening teeth of claim 1, wherein the patch further comprises a polyphosphate.

6. The patch for whitening teeth of claim 5, wherein the polyphosphate is selected from the group consisting of tetrasodium pyrophosphate, sodium acid pyrophosphate, sodium hexametaphophate, sodium tripolyphosphate, sodium potassium tripolyphosphate, tetrapotassium pyrophosphate, acidic sodium metapolyphosphate, acidic sodium polyphosphate and combinations thereof.

7. The patch for whitening teeth of claim 1, wherein the backing layer comprises a water-insoluble polymer selected from the group consisting of cellulose acetate phthalate, polyvinyl acetate, ethyl cellulose, polymethylmethacrylate, a methacryloylethyl betain/methacrylate copolymer, a methacrylic acid copolymer, an aminoalkylmethacrylate copolymer and mixtures thereof.

8. The patch for whitening teeth of claim 1, wherein the backing layer comprises a base polymer selected from the group consisting of polyethylene, ethylvinyl acetate, ethylvinyl alcohol, polyester, polyurethane and combinations thereof.

9. The patch for whitening teeth of claim 1, wherein a peroxide activator is contained in a layer which contains no peroxide.

10. The patch for whitening teeth of claim 9, wherein the peroxide activator is selected from the group consisting of Fe, a Fe salt, Cu, a Cu salt, Ca, a Ca salt, Mn, Mn salts, Pt, a Pt salt, Pd, a Pd salt, Ag, a Ag salt, manganese gluconate, sodium bicarbonate, sodium hydroxide, activated charcoal and combinations thereof.

11. The patch for whitening teeth of claim 1, wherein the patch further comprises a protective layer between the contact adhesive layer and the active material reservoir layer and the contact adhesive layer comprises a peroxide activator.

12. The patch for whitening teeth of claim 1, wherein a flavor is added to one or more of the contact adhesive layer, the active material reservoir layer and the backing layer.

13. A dry patch for whitening teeth having a multi-layer structure of three or more layers comprising a contact adhesive layer, a backing layer, and an active material reservoir layer comprising a peroxide and a hydrophilic glass polymer selected from the group consisting of polyvinyl pyrrolidone-vinyl acetate copolymer, polyethylene oxide, polyvinyl pyrrolidone, Polyquaterium-11, Polyquaterium-39, and combinations thereof, which is positioned between the contact adhesive layer and the backing layer;

wherein the contact adhesive layer is substantially free of peroxide and comprises a hydrophilic glass polymer as a base polymer; and wherein the contact adhesive layer provides substantial adhesive attachment to the teeth when hydrated by water and placed in contact with the teeth and has insubstantial adhesiveness before hydration and attachment to the teeth, and the active material reservoir layer releases peroxide contained therein subsequent to the hydration and attachment of the contact adhesive layer to the teeth.

14. The patch for whitening teeth of claim 13, wherein the peroxide is selected from the group consisting of hydrogen peroxide, carbamide peroxide, calcium peroxide, sodium percarbonate, sodium perborate, tetrasodium pyrophosphate peroxidate and combinations thereof.

15. The patch for whitening teeth of claim 13, wherein the patch further comprises a polyphosphate.

16. The patch for whitening teeth of claim 15, wherein the polyphosphate is selected from the group consisting of tetrasodium pyrophosphate, sodium acid pyrophosphate, sodium hexametaphophate, sodium tripolyphosphate, sodium potassium tripolyphosphate, tetrapotassium pyrophosphate, acidic sodium metapolyphosphate, acidic sodium polyphosphate, and combinations thereof.

17. The patch for whitening teeth of claim 13, wherein the backing layer comprises a water-insoluble polymer selected from the group consisting of cellulose acetate phthalate, polyvinyl acetate, ethyl cellulose, polymethylmethacrylate, a methacryloylethyl betain/methacrylate copolymer, a methacrylic acid copolymer, a aminoalkylmethacrylate copolymer and mixtures thereof.

18. The patch for whitening teeth of claim 13, wherein the backing layer comprises a base polymer selected from the group consisting of polyethylene, ethylvinyl acetate, ethylvinyl alcohol, polyester, polyurethane, and combinations thereof.

19. The patch for whitening teeth of claim 13, wherein a peroxide activator is contained in a layer which contains no peroxide.

20. The patch for whitening teeth of claim 19, wherein the peroxide activator is selected from the group consisting of Fe, a Fe salt, Cu, a Cu salt, Ca, a Ca salt, Mn, Mn salts, Pt, a Pt salt, Pd, a Pd salt, Ag, a Ag salt, manganese gluconate, sodium bicarbonate, sodium hydroxide, activated charcoal and combinations thereof.

21. The patch for whitening teeth of claim 13, wherein the patch further comprises a protective layer between the contact adhesive layer and the active material reservoir layer and the contact adhesive layer comprises a peroxide activator.

22. The patch for whitening teeth of claim 13, wherein a flavor is added to one or more of the contact adhesive layer, the active material reservoir layer and the backing layer.

* * * * *